US00PP31529P2

(12) United States Plant Patent
Olesen et al.

(10) Patent No.: US PP31,529 P2
(45) Date of Patent: Mar. 10, 2020

(54) ***CLEMATIS* PLANT NAMED 'EVIPO085'**

(50) Latin Name: *Clematis viticella*
Varietal Denomination: Evipo085

(71) Applicants: Mogens Nyegaard Olesen, Fredensborg (DK); Raymond J. Evison, St Sampsons Vale (GB)

(72) Inventors: Mogens Nyegaard Olesen, Fredensborg (DK); Raymond J. Evison, St Sampsons Vale (GB)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 15/999,908

(22) Filed: Sep. 10, 2018

(51) Int. Cl.
*A01H 5/02* (2018.01)
*A01H 6/72* (2018.01)

(52) U.S. Cl.
USPC ..... Plt./228
CPC ..... *A01H 6/72* (2018.05)

(58) Field of Classification Search
USPC ..... Plt./228
CPC ..... A01H 6/72
See application file for complete search history.

*Primary Examiner* — Keith O. Robinson

(57) ABSTRACT

A new *Clematis* plant with a compact growth habit, profuse, violet-purple flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

1 Drawing Sheet

Botanical classification:
Genus: *Clematis.*
Species: *viticella.*
Variety denomination: 'Evipo085'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 2006 and the resulting seeds were planted the following winter in a controlled environment in Guernsey, Channel Islands, United Kingdom. The new variety named 'Evipo085' originated as a single seedling from the stated cross.

The new *Clematis* plant may be distinguished from its female seed parent and male pollen parent by the following characteristics. The female seed parent has a growth height of about 55 cm, while the new variety has a growth height of about 25 cm. The male seed parent has light purple tepals while the new variety has violet-purple tepals.

The objective of the hybridization of this *Clematis* plant was to create a new and distinct variety for nursery culture with unique qualities such as:

1. Uniform and abundant violet-purple flowers;
2. Vigorous and compact growth, making the variety suitable for container culture; and
3. Improved disease resistance.

This combination of qualities was lacking in *Clematis* plants that were in commercial cultivation and the qualities have been substantially achieved in the new variety.

'Evipo085' was selected by Mogens N. Olesen and Raymond J. Evison in their *Clematis* development program in the Channel Islands, United Kingdom in 2007. Asexual reproduction of 'Evipo085' by means of vegetative stem cuttings and traditional layering was first performed by Mogens N. Olesen and Raymond J. Evison in the nursery during the summer of 2007. This initial and subsequent asexual propagations have demonstrated that the characteristics of 'Evipo085' are true to type and are transmitted from one generation to the next.

BRIEF DESCRIPTION OF THE DRAWING

The accompanying color illustration shows as true as is reasonably possible to obtain in color photographs of this type the typical characteristics of the buds, flowers, leaves, and stems, of 'Evipo085'. Specifically illustrated in the drawing is a flowering vine showing even and abundant flower bud development at each axillary bud, open flowers viewed from above and beneath, tepals detached, reproductive flower parts, and leaves. Illustrated plants are 2 years of age.

DETAILED DESCRIPTION OF THE VARIETY

The following is a detailed description of 'Evipo085', as observed in its growth throughout the flowering period in Marion County Oreg. Observed plants were cultivated for a period of 24 months in an open field. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *Clematis* variety 'Evipo030' described and illustrated in U.S. Plant Pat. No. 15,991 are compared to 'Evipo085' in Chart 1.

CHART 1

| | 'Evipo085' | 'Evipo030' |
|---|---|---|
| Flower diameter | 75 to 88 mm | 70 to 90 mm |
| Tepal upper surface after opening | Violet Group N88B at the central bar with marginal intonations of Violet Group N88A | Violet Group N88C |
| Tepal count | 7 to 10 | 6 to 8 |

FLOWER AND FLOWER BUD

Blooming habit: Continuous. The natural flowering period is generally from April to September. Flowering occurs on new growth only.

Flower bud:
- *Size*.—Normally 28 mm in length. Bud diameter is 13 mm.
- *Bud form*.—Ovate.
- *Bud color*.—Yellow-Green Group 145C.
- *Texture*.—Pubescent.

Pedicel:
- *Surface texture*.—Pubescent.
- *Length*.—On average 15 mm in length with 2 mm diameter.
- *Color*.—Yellow-Green Group 144B.
- *Strength*.—Strong.

Receptacle:
- *Surface texture*.—Lightly pubescent.
- *Shape*.—Broad funnel.
- *Size*.—1 mm (h)×3 mm (w).
- *Color*.—Yellow-Green Group 144B.

Flower arrangement:
- *Location on vine*.—New and old growth.
- *Arrangement*.—At each axillary bud, flowers are borne in clusters of 2 to 3, or singly.

Flower bloom:
- *Size*.—75 to 88 mm in diameter and 15 mm in depth.
- *Profile*.—Open flowers are almost flat.
- *Fragrance*.—None.
- *Lasting quality*.—Flowers normally remain up to 10 days on the plant.
- *Attitude*.—Flowers are oriented upwards.

Tepals:
- *Tepal color*.—Upon opening, the upper surface is Violet Group N88B at the central bar with marginal intonations of Violet Group N88A. The lower surface is Yellow-Green Group 145C at the central bar, with Violet Group 85B and other intonations Violet Group N88B at the margins.
- *Quantity*.—Normally 7 to 10 tepals.
- *Size*.—About 43 mm in length by 25 mm wide.
- *Shape*.—Individual tepal shape is elliptic. The tepal apex is mucronate. The tepal base is slightly acute.
- *Apex recurvature*.—None.
- *Tepal cross section*.—Reflexed/Slightly reflexed/flat/slightly cupped/cupped.
- *Margins*.—Entire with slight reflex. Moderate undulations of margin observed.
- *Persistence*.—Tepals drop off cleanly.
- *Arrangement*.—Overlapping.

Reproductive organs:
- *Pollen*.—None observed.
- *Anthers*.—Size: 5 mm in length. Color: Green-White Group 157A with intonations of Brown Group 200A. Quantity: On average, 40.
- *Filaments*.—Color: Green-White Group 157B. Length: 6 mm.
- *Pistils*.—Quantity: On average, 15.
- *Styles*.—Color: Green-White Group 157B. Length: 10 mm.

Seed head characteristics: Seed not observed to date.

PLANT

Plant form: Low growing, spreading, compact and non-climbing.

Plant growth: Compact.

Size: Seasons growth attains about 25 cm in height. Average spread is 50 cm.

Stems:
- *Color*.—Juvenile stems are Yellow-Green Group 144B. Mature stems are Yellow-Green Group 144B with intonations of Greyed-Purple Group 183B.
- *Internodes*.—On average, 35 mm between nodes.
- *Length*.—Normally 5 cm from the base of the plant to the flowering portion of the stem.
- *Diameter*.—About 3.5 mm.
- *Texture*.—Mature stems are smooth or slightly ribbed.

Plant foliage:
- *Leaf characteristics*.—Deciduous.
- *Arrangement*.—Ternate.
- *Leaf size*.—Compound leaves are about 120 mm (l)× 120 mm (w). Leaflets are about 55 mm (l)×37 mm (w).
- *Abundance*.—On average there are leaves per 10 cm of stem.
- *Leaf color*.—Juvenile upper Yellow-Green Group 144B. Juvenile lower Yellow-Green Group 144B. Mature upper Yellow-Green Group 146A. Mature lower Yellow-Green Group 147B.
- *Stipules*.—Absent.
- *Petioles*.—Size: Normally 40 mm in length by 2 mm diameter. Texture: Smooth. Color: Yellow-Green Group 144B with intonations of Greyed-Orange Group 176A.
- *Petioloule*.—Size: About 15 mm in length by 2 mm diameter. Texture: Smooth. Color: Yellow-Green Group 144B with intonations of Greyed-Orange Group 176A.
- *Leaflet shape*.—Cordate. The base is rounded, apex acute.
- *Margin*.—Entire.
- *Surface*.—The upper side is smooth, the lower side is smooth.
- *Thickness*.—Moderate.
- *Glossiness*.—Not glossy.

Disease resistance: Subject to any disease that normally attacks the species. However the variety is more tolerant to *Clematis* wilt, *Ascochyta clematidina*, than some *Clematis* known to the inventors.

Cold hardiness: The variety is tolerant to USDA Hardiness Zone 6.

Heat tolerance: The variety has been found to be suitable for climate conditions found in the American Horticulture Society heat zone 7.

We claim:

1. A new and distinct variety of *Clematis* plant named 'Evipo085', substantially as described and illustrated, due to its abundant violet-purple flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

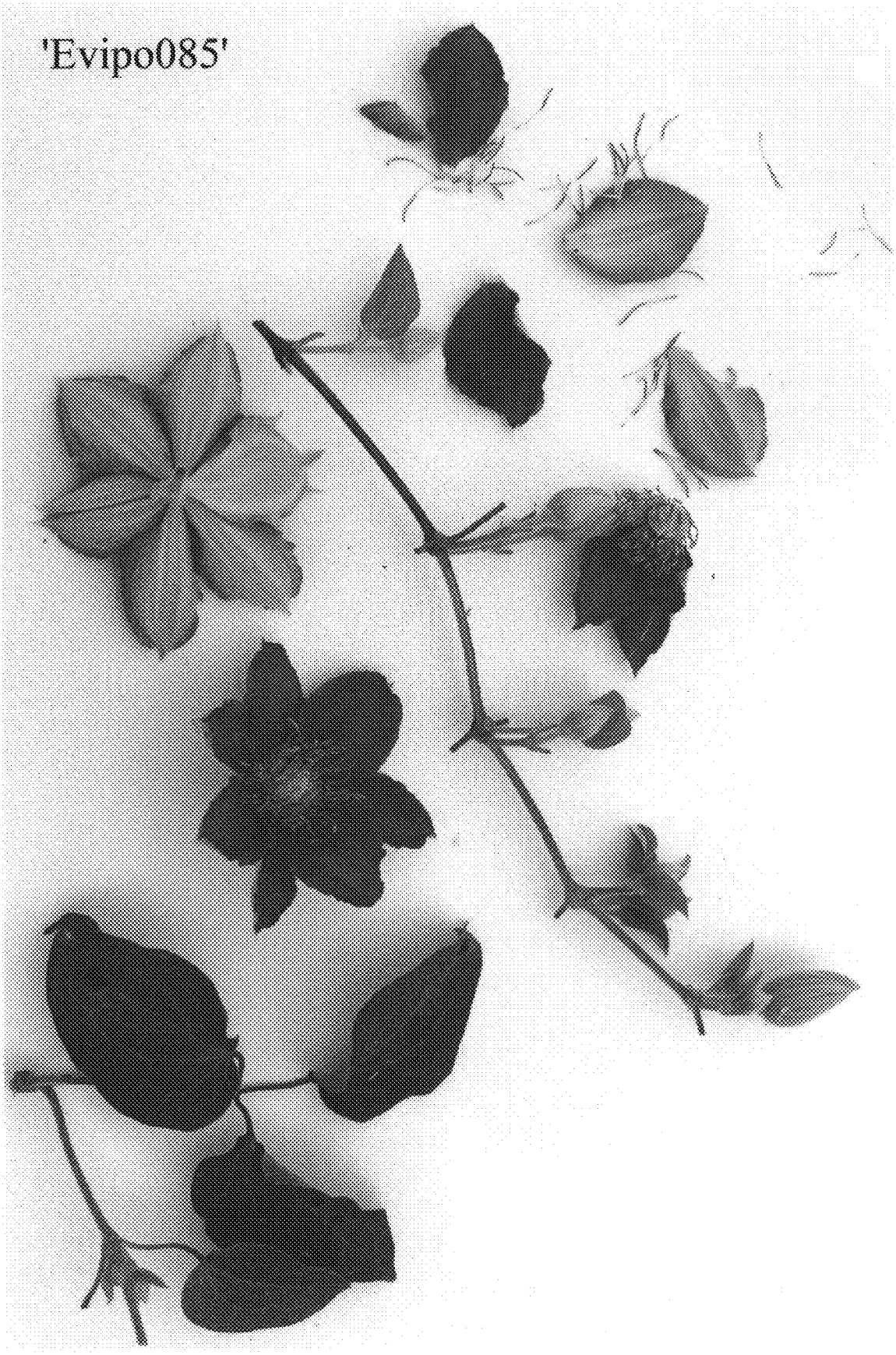
'Evipo085'